United States Patent [19]

Fesik et al.

[11] Patent Number: 6,043,024
[45] Date of Patent: Mar. 28, 2000

[54] USE OF ONE-DIMENSIONAL NUCLEAR MAGNETIC RESONANCE TO IDENTIFY LIGANDS TO TARGET BIOMOLECULES

[75] Inventors: Stephen W. Fesik, Gurnee; Philip J. Hajduk, Palatine; Edward T. Olejniczak, Grayslake, all of Ill.

[73] Assignee: Abbott Laboratories, Abbott Park, Ill.

[21] Appl. No.: 08/844,124

[22] Filed: Apr. 18, 1997

[51] Int. Cl.$^7$ ...................................................... C12Q 1/68
[52] U.S. Cl. .................................. 435/4; 422/50; 422/62; 422/68.1; 422/69; 422/82.01; 435/5; 435/6; 435/7.1; 435/286.1; 435/287.1; 435/287.2; 435/289.1; 435/810; 436/501; 935/77; 935/78; 935/88
[58] Field of Search ........................... 435/5, 6, 7.1, 810, 435/4, 286.1, 287.1, 287.2, 289.1; 436/501; 935/77, 78, 88; 422/50, 62, 68.1, 69, 82.01

[56] References Cited

U.S. PATENT DOCUMENTS 5,698,401  12/1997  Fesik et al. ............................. 435/7.1
5,804,390   9/1998  Fesik et al. ............................. 435/7.1

OTHER PUBLICATIONS

M. Liu et al., "High Resolution Diffusion and Relaxation Edited One–and Two–Dimensional 1 H NMR Spectroscopy of Biological Fluids", Anal.Chem., vol. 68 (No. 19), p. 3370–3376 (1996).

M. Lin et al., "Mixture Analysis in Combinatorial Chemistry. Application of Diffusion–Resolved NMR Spectroscopy", J. Org. Chem, Vol. 61 (No. 21), p. 7617–7619, (1996).

C. Rossi et al., "Nuclear magnetic resonance as a tool for the identification of specific DNA–ligand interaction", Chemical Physics Letters, vol. 189 (No. 3), p. 278–280, (1992).

S. Meiboom et al., "Modified Spin–Echo Method for Measuring Nuclear Relaxation Times", *The Review of Scientific Instruments*, Vol. 29, No. 8, (1958) 688–691.

T.M. Logan et al., "Structural Characterization of the FK506 Binding Protein Unfolded in Urea and Guanidine Hydrochloride," *Journal of Molecular Biology*, Vol. 236, (1994) 637–648.

A.S. Altieri et al., "Association of Biomolecular Systems Via Pulsed Field Gradient NMR Self–Diffusion Measurments," *Journal of the American Chemical Society*, Vol. 117, (1995) 7566–7567.

S.B. Shuker et al., "Discovering High–Affinity Ligands for Proteins: SAR by NMR," *Science*, Vol. 274, (1996) 1531–1534.

S.J. Gibbs et al., "A PFG NMR Experiment for Accurate Diffusion and Flow Studies in the Presence of Eddy Currents," *Journal of Magnetic Resonance*, Vol. 93, (1991) 395–402.

*Primary Examiner*—Ardin H. Marschel

[57] ABSTRACT

The present invention provides a process for identifying compounds which bind to a specific target molecule. The process comprises the steps of: a) generating a first $T_2$- or diffusion-filtered proton spectrum of one or a mixture of chemical compounds; b) exposing one or a mixture of chemical compounds to the target molecule; c) generating a second $T_2$- or diffusion-filtered proton spectrum of one or a mixture of chemical compounds that has been exposed the target molecule in step (b); and d) comparing said first and second $T_2$- or diffusion-filtered proton spectra to determine differences between said first and said second spectra, the differences identifying the presence of one or more compounds that are ligands which have bound to the target molecule.

17 Claims, 6 Drawing Sheets

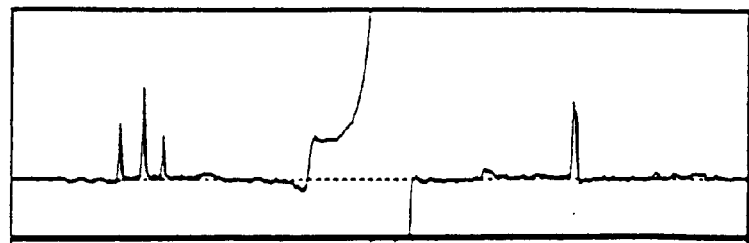
FIG. 1A
FIG. 1B
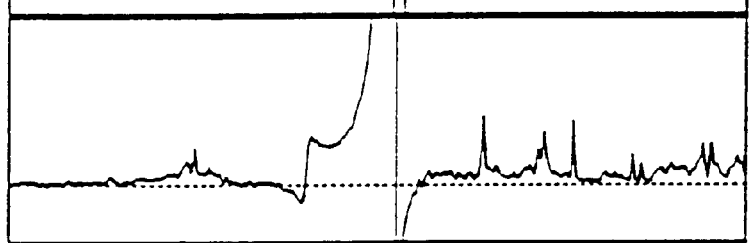
FIG. 1C
FIG. 1D
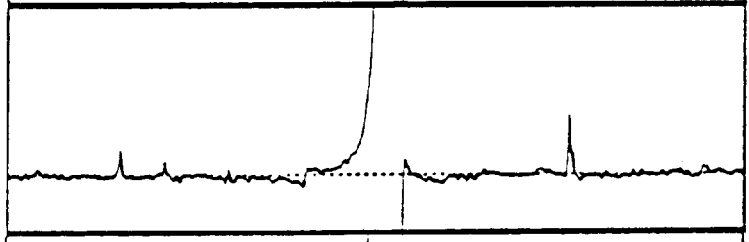
FIG. 1E
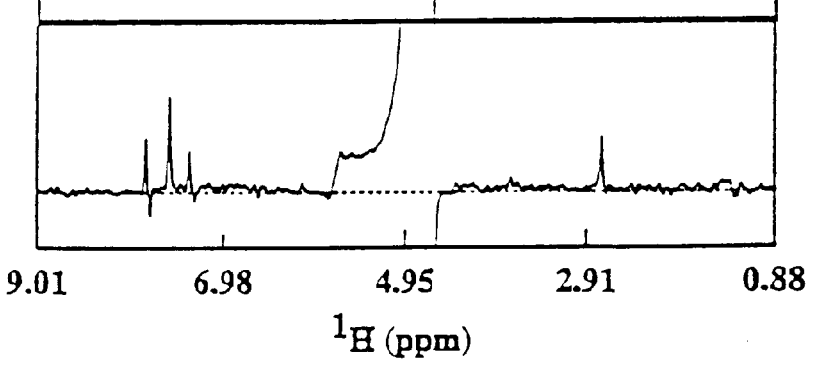

$^1$H (ppm)

$^1$H (ppm)

6,043,024

USE OF ONE-DIMENSIONAL NUCLEAR MAGNETIC RESONANCE TO IDENTIFY LIGANDS TO TARGET BIOMOLECULES

TECHNICAL FIELD OF THE INVENTION

The present invention pertains to a method for the screening of compounds for binding to target biomolecules using one-dimensional nuclear magnetic resonance (NMR) spectroscopy.

BACKGROUND OF THE INVENTION

One of the most powerful tools for discovering new drug leads is random screening of synthetic chemical and natural product databases to discover compounds that bind to a particular target molecule (i.e., the identification of ligands of that target). Using this method, ligands may be identified by their ability to form a physical association with a target molecule or by their ability to alter a function of a target molecule.

When physical binding is sought, a target molecule is typically exposed to one or more compounds suspected of being ligands and assays are performed to determine if complexes between the target molecule and one or more of those compounds are formed. Such assays, as is well known in the art, test for gross changes in the target molecule (e.g., changes in size, charge, mobility) that indicate complex formation.

Where functional changes are measured, assay conditions are established that allow for measurement of a biological or chemical event related to the target molecule (e.g., enzyme catalyzed reaction, receptor-mediated enzyme activation). To identify an alteration, the function of the target molecule is determined before and after exposure to the test compounds.

Existing physical and functional assays have been used successfully to identify new drug leads for use in designing therapeutic compounds. There are, however, limitations inherent to those assays that compromise their accuracy, reliability and efficiency.

A major shortcoming of existing assays relates to the problem of "false positives". In a typical functional assay, a "false positive" is a compound that triggers the assay but which compound is not effective in eliciting the desired physiological response. In a typical physical assay, a "false positive" is a compound that, for example, attaches itself to the target but in a non-specific manner (e.g., non-specific binding). False positives are particularly prevalent and problematic when screening higher concentrations of putative ligands because many compounds have non-specific affects at those concentrations.

In a similar fashion, existing assays are plagued by the problem of "false negatives", which result when a compound gives a negative response in the assay but which compound is actually a ligand for the target. False negatives typically occur in assays that use concentrations of test compounds that are either too high (resulting in toxicity) or too low relative to the binding or dissociation constant of the compound to the target.

It has recently been demonstrated that two-dimensional $^{15}N/^1H$ spectral analysis can be used to identify compounds which bind to a target protein, and this approach overcomes many of the problems associated with other existing assays for ligand identification. However, this approach requires that the protein be $^{15}N$-labeled, soluble and well-behaved up to concentrations of 0.3 mM or higher. Furthermore, only proteins which give rise to analyzeable $^{15}N/^1H$ correlation maps can be used with this method, which, with current technology, limits the molecular weight of the target protein to less than 40 kDa. In addition, the method is time-consuming in that compounds are tested in combinations of 10, and, when it has been determined that at least one of the compounds in the mixture is active, each compound must be individually tested for binding to the target protein.

Because of the problems inherent to existing screening methods, there continues to be a need to provide new, rapid, efficient, accurate and reliable means of screening compounds to identify and design ligands that specifically bind to a particular target.

BRIEF SUMMARY OF THE INVENTION

In one aspect, the present invention provides a process of screening compounds for biological activity to identify ligands that bind to a specific target molecule. That process comprises the steps of: a) generating a first $T_2$- or diffusion-filtered proton spectrum of one or a mixture of chemical compounds; b) exposing one or a mixture of chemical compounds to the target molecule; c) generating a second $T_2$- or diffusion-filtered proton spectrum of one or a mixture of chemical compounds that has been exposed to the target molecule in step (b); and d) comparing said first and second $T_2$- or diffusion-filtered proton spectra to determine differences between said first and said second spectra, the differences identifying the presence of one or more compounds that are ligands which have bound to the target molecule.

Where the process of the present invention screens more than one compound in step (b), that is, a mixture of compounds, and where a difference between the first spectrum generated from the mixture and that generated from the mixture in the presence of the target molecule, the active compound can be identified immediately if the spectrum of the active compound in the absence of the target molecule is known. This is because the differences observed between the spectra in step (d) will occur at the chemical shifts of the active compound. Additional steps can be performed to identify which specific compound or compounds contained in the mixture is binding to the target molecule, either in the absence of known chemical shift information for the compounds in said mixture or to confirm binding. Those additional steps comprise the steps of e) generating a $T_2$- or diffusion-filtered proton spectrum of each compound in the mixture f) exposing each compound in the mixture individually to the target molecule, g) generating a $T_2$- or diffusion-filtered proton spectrum of each compound in the mixture after exposure to the target molecule h) comparing each spectrum generated in step g) to the first spectrum generated from the target molecule alone to determine differences in any of those compared spectra, the differences identifying the presence of a compound that is a ligand which has bound to the target molecule.

An advantage of the present invention is the capability of the process of the present invention to determine the binding of potential ligands to an unlabeled target molecule of any size or composition, provided that the size of the target is sufficiently larger than the potential ligand so as to cause changes in its relaxation or diffusion rates upon binding to the target molecule.

Another advantage of the present invention is the capability of the process of the present invention to determine the binding of even weakly binding ligands to the target molecule.

A further advantage of the present invention is the capability of the process of the present invention to identify an active compound or compounds in a mixture of compounds by direct comparison of the chemical shifts in the difference spectra to the known chemical shifts of the compounds comprising the mixture in the absence of the target biomolecule.

In this preferred embodiment, the process of determining binding of a ligand can be performed in the presence of a second bound ligand. In accordance with this embodiment, the target molecule is bound to that second ligand before exposing that target to the test compounds.

This method uses a $T_2$- or diffusion filtered proton spectroscopic screening process as set forth above to identify a first and subsequent ligands that bind to the target molecule. A complex of the target molecule and two or more ligands is formed and structural data is obtained preferably using NMR spectroscopy or X-ray crystallography. That structural data is used to determine the spatial orientation of the ligands relative to each other and to the target molecule.

Based on the spatial orientation, the ligands are linked together to form a high-affinity ligand which is useful as a ligand to the particular target molecule and is useful as a potential pharmaceutically active drug. The selection of an appropriate linking group is made by maintaining the spatial orientation of the ligands to one another and to the target molecule based upon principles of bond angle and bond length information well known in the organic chemical art. The linking procedure or synthetic scheme to combine the at least two ligands to form the high-affinity ligand is performed by well known synthetic procedures and/or retrosynthetic analysis. The high-affinity ligand may be prepared by any means which actually produces the final ligand and is not limited to simply linking the two ligands together through a linking group. Any linear synthesis or convergent synthetic method may be utilized to form the final product. Once the at least two ligands which have affinity to the target molecule (preferably a protein) are found, the high-affinity ligand is designed and made by methods well known to those of skill in the art. The ligands are selected from the diverse pool of small molecules having diverse atoms and molecular arrangements, stereochemistry etc. The limiting factor is that the at least two ligands have some affinity as a ligand to at least one site on the polypeptide or target molecule. The screening process disclosed herein, however, can identify a single ligand or a plurality of ligands which can also be manipulated by traditional drug design methods to form pharmaceutically active products or can be utilized in the drug design process disclosed herein to link at least two ligands to form a high-affinity ligand.

Thus, the molecular design method comprises identifying a first ligand moiety to the target molecule using one-dimensional T2- or diffusion-filtered spectroscopy; identifying subsequent ligand moieties to the target molecule using one-dimensional T2- or diffusion-filtered spectroscopy; forming a complex of the first and subsequent ligand moieties to the target molecule; obtaining structural data on the complex and, thus, the spatial orientation of the first and subsequent ligand moieties on the target molecule; and linking the first and subsequent ligand moieties to form the high-affinity ligand which may also be a pharmaceutically active drug while maintaining the spatial orientation of the ligand moieties.

The identification of subsequent ligand moieties can be performed in the absence or presence of the first ligand (e.g., the target molecule can be bound to the first ligand before being exposed to the test compounds for identification of the second ligand).

In a preferred embodiment, the target molecule used in a screening or design process is a polypeptide. The polypeptide target is preferably produced in recombinant form from a host cell transformed with an expression vector that contains a polynucleotide that encodes the polypeptide.

BRIEF DESCRIPTION OF THE DRAWINGS

In the drawings which form a portion of the specification:

FIG. 1A shows a $T_2$-filtered spectrum of compound 1 in aqueous buffer.

FIG. 1B shows a $T_2$-filtered spectrum of compound in the presence of FKBP.

FIG. 1C shows a $T_2$-filtered spectrum of FKBP.

FIG. 1D shows a difference spectrum obtained by subtracting FIG. 1C from FIG. 1B.

FIG. 1E shows a difference spectrum obtained by subtracting FIG. 1D from FIG. 1A.

For all experiments, the $T_2$-filter spin-lock time was 200 ms with a spin-echo delay of 1 ms, the concentration of compound 1 was 100 $\mu$M, the concentration of FKBP was 50 $\mu$M, and the buffer was 50 mM $PO_4$, 100 mM NaCl, pH 6.5 (95% $D_2O$).

Figure 2A:
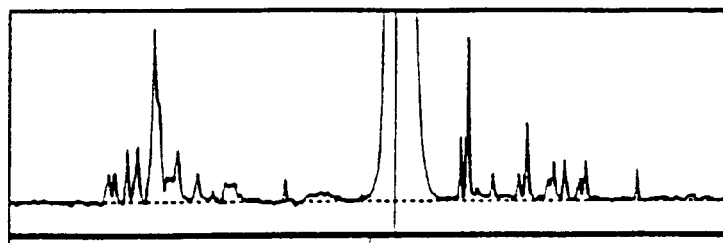

FIG. 2A shows a $T_2$-filtered spectrum of a mixture of compounds 1–9.

Figure 2B:
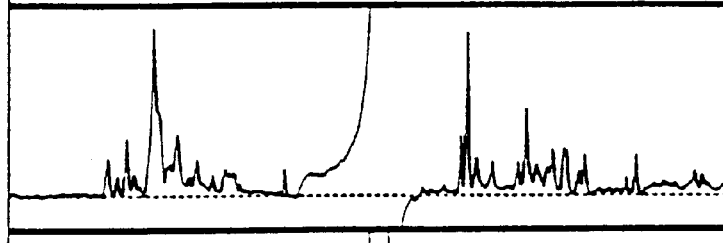

FIG. 2B shows a $T_2$-filtered spectrum of a mixture of compounds 1–9 in the presence of FKBP.

Figure 2C:
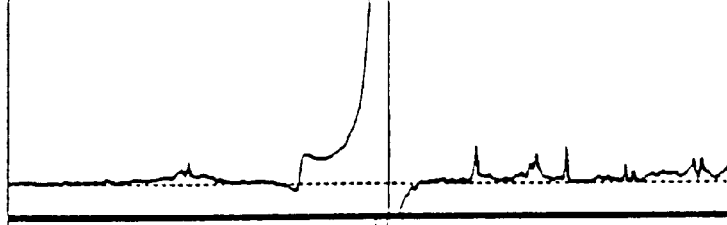

FIG. 2C shows a $T_2$-filtered spectrum of FKBP.

Figure 2D:
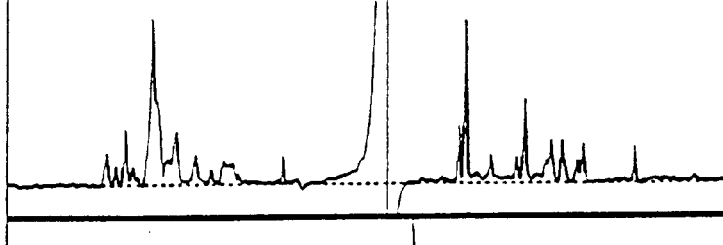

FIG. 2D shows a difference spectrum obtained by subtracting FIG. 2C from FIG. 2B.

Figure 2E:

FIG. 2E shows a difference spectrum obtained by subtracting FIG. 2D from FIG. 2A.

Figure 2F:
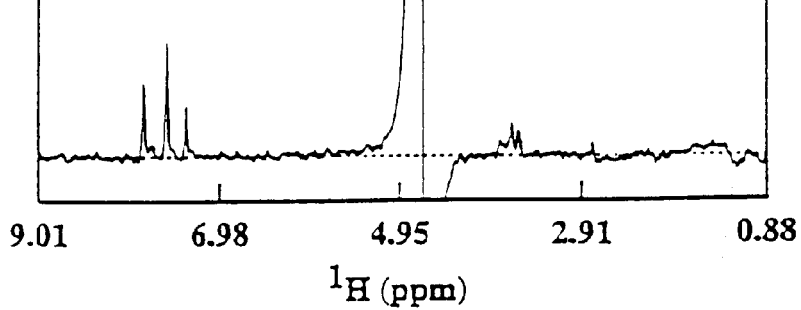

FIG. 2F shows a reference $T_2$-filtered spectrum of compound 1 alone.

For all experiments, the $T_2$-filter spin-lock time was 200 ms with a spin-echo delay of 1 ms, the concentration of all chemical compounds was 100 $\mu$M, the concentration of FKBP was 50 $\mu$M, and the buffer was 50 mM $PO_4$, 100 mM NaCl, pH 6.5 (95% $D_2O$).

Figure 3A:

FIG. 3A shows a $T_2$-filtered spectrum of a mixture of compounds 2–9.

Figure 3B:
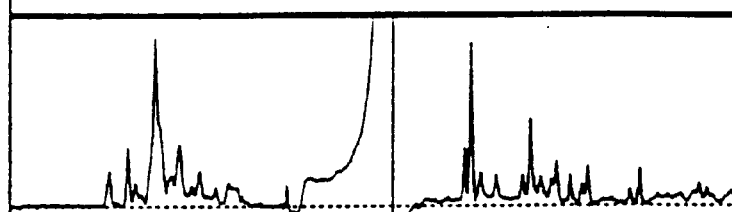

FIG. 3B shows a $T_2$-filtered spectrum of a mixture of compounds 2–9 in the presence of FKBP.

Figure 3C:
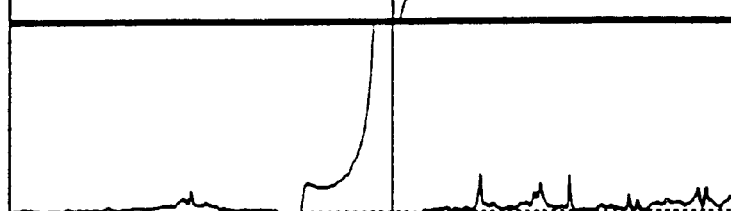

FIG. 3C shows a $T_2$-filtered spectrum of a mixture of FKBP.

Figure 3D:
Figure 4A:
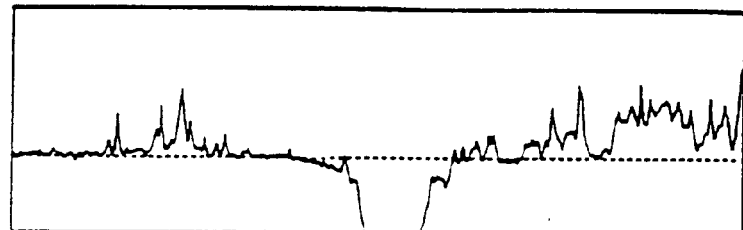
Figure 4B:
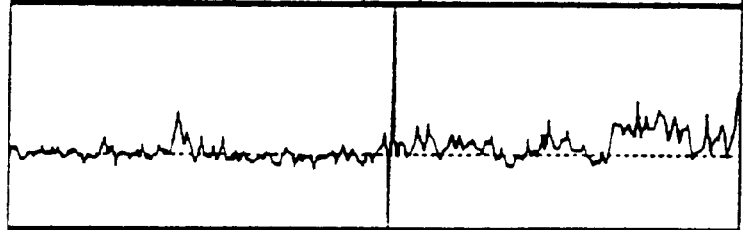
Figure 4C:

FIG. 3D shows a difference spectrum obtained by subtracting FIG. 4C from FIG. 3B.

Figure 3E:
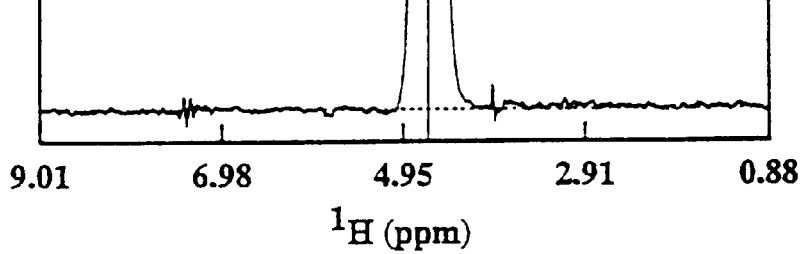

FIG. 3E shows a difference spectrum obtained by subtracting FIG. 3D from FIG. 3A.

For all experiments, the $T_2$-filter spin-lock time was 200 ms with a spin-echo delay of 1 ms, the concentration of all chemical compounds was 100 $\mu$M, the concentration of FKBP was 50 $\mu$M, and the buffer was 50 mM $PO_4$, 100 mM NaCl, pH 6.5 (95% $D_2O$).

FIG. 4A shows a diffusion-filtered spectrum of compound 1 in the presence of FKBP using a low gradient strength.

FIG. 4B shows a diffusion filtered spectrum of compound 1 in the presence of FKBP using a high gradient strength.

FIG. 4C shows a difference spectrum obtained by subtracting FIG. 4B from FIG. 4A.

Figure 4D:

FIG. 4D shows a diffusion-filtered spectrum of compound 1 using a low gradient strength.

Figure 4E:
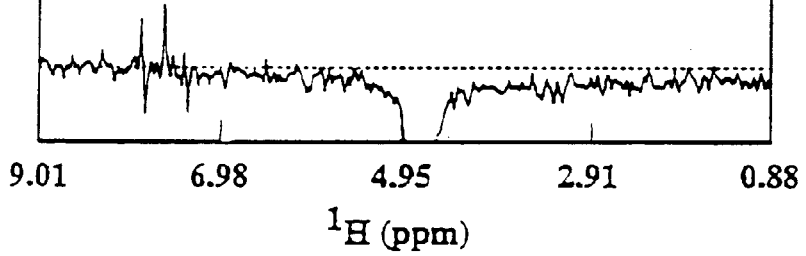

FIG. 4E shows a difference spectrum obtained by subtracting FIG. 4C from FIG. 4D.

For all experiments, low and high gradient strengths correspond to 3 and 48 Gauss/cm, respectively. The high gradient strength was sufficient to eliminate the residual HDO signal in the sample. A diffusion delay time of 300 ms was used, the concentration of all chemical compounds was 100 $\mu$M, the concentration of FKBP was 50 $\mu$M, and the buffer was 50 mM $PO_4$, 100 mM NaCl, pH 6.5 (95% $D_2O$).

Figure 5A:

FIG. 5A shows a diffusion-filtered spectrum of a mixture of compounds 1–9 in the presence of FKBP using a low gradient strength.

Figure 5B:
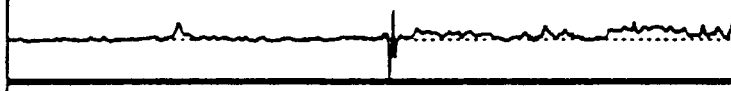

FIG. 5B shows a diffusion filtered spectrum of a mixture of compounds 1–9 in the presence of FKBP using a high gradient strength.

Figure 5C:
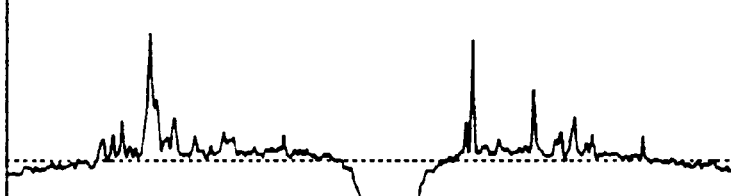

FIG. 5C shows a difference spectrum obtained by subtracting FIG. 5B from FIG. 5A.

Figure 5D:
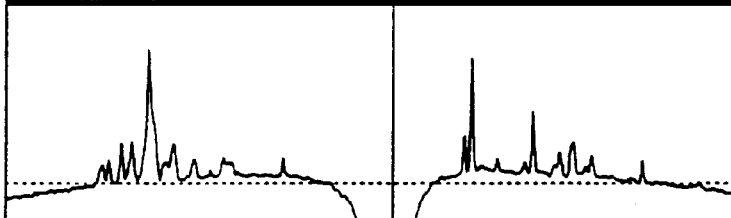

FIG. 5D shows a diffusion-filtered spectrum of a mixture of compounds 1–9 using a low gradient strength.

Figure 5E:
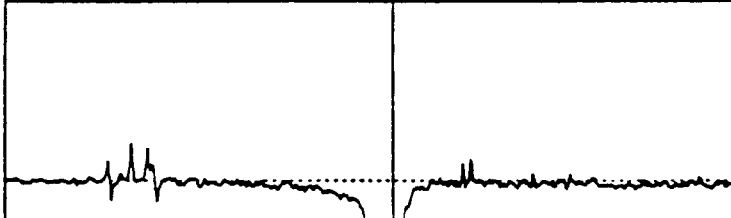

FIG. 5E shows a difference spectrum obtained by subtracting FIG. 5C from FIG. 5D.

Figure 5F:
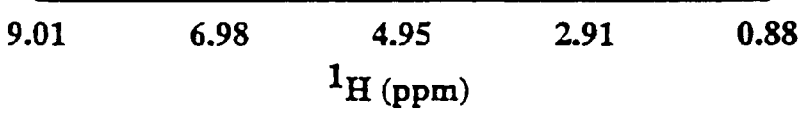

FIG. 5F shows a reference spectrum of compound 1 alone.

For all experiments, low and high gradient strengths correspond to 3 and 48 Gauss/cm, respectively. The high gradient strength was sufficient to eliminate the residual HDO signal in the sample. A diffusion delay time of 300 ms was used, the concentration of all chemical compounds was 100 $\mu$M, the concentration of FKBP was 50 $\mu$M, and the buffer was 50 mM $PO_4$, 100 mM NaCl, pH 6.5 (95% $D_2O$).

Figure 6A:
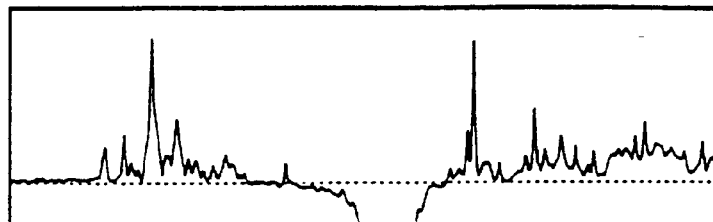

FIG. 6A shows a diffusion-filtered spectrum of a mixture of compounds 2–9 in the presence of FKBP using a low gradient strength.

Figure 6B:
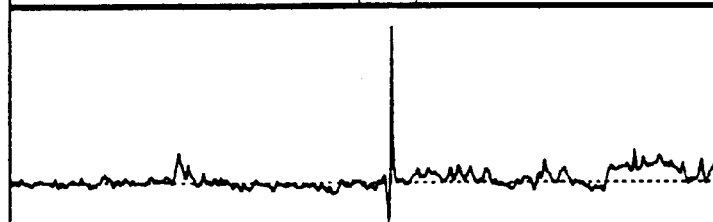

FIG. 6B shows a diffusion filtered spectrum of a mixture of compounds 2–9 in the presence of FKBP using a high gradient strength.

Figure 6C:
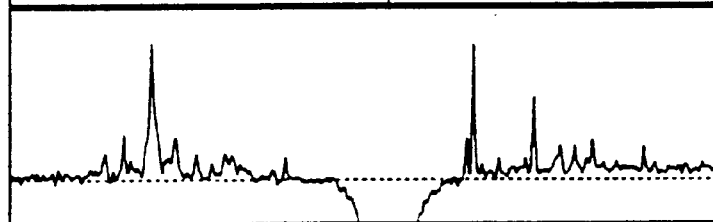

FIG. 6C shows a difference spectrum obtained by subtracting FIG. 6B from FIG. 6A.

Figure 6D:
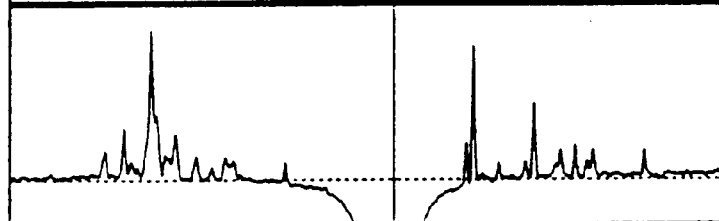

FIG. 6D shows a diffusion-filtered spectrum of a mixture of compounds 2–9 using a low gradient strength.

Figure 6E:
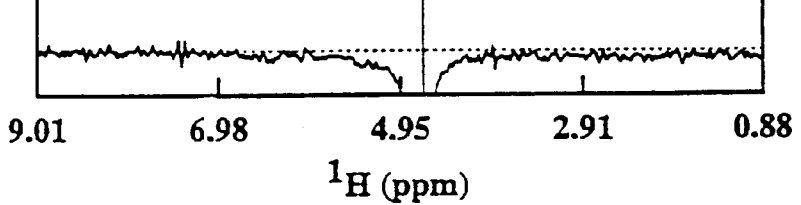

FIG. 6E shows a difference spectrum obtained by subtracting FIG. 6C from FIG. 6D.

For all experiments, low and high gradient strengths correspond to 3 and 48 Gauss/cm. respectively. The high gradient strength was sufficient to eliminate the residual HDO signal in the sample. A diffusion delay time of 300 ms was used, the concentration of all chemical compounds was 100 $\mu$M, the concentration of FKBP was 50 $\mu$M, and the buffer was 50 ml $PO_4$, 100 mM NaCl, pH 6.5 (95% $D_2O$).

DETAILED DESCRIPTION OF THE INVENTION

The present invention provides a rapid and efficient screening method for identifying ligands that bind to therapeutic target molecules.

Ligands are identified by testing the binding of molecules to a target molecule (e.g., protein, nucleic acid, etc.) by following, with nuclear magnetic resonance (NMR) spectroscopy, the changes in either the relaxation or diffusion rates of the ligand resonances upon the addition of the target. The pool of screened molecules may be selected from a compound collection such as those currently available in most pharmaceutical companies or university laboratories.

Information about the structure/activity relationships between ligands identified by such a process can then be used to design new drugs that serve as ligands to the target molecule. By way of example, where two or more ligands to a given target molecule are identified, a complex of those ligands and the target molecule is formed. The spatial orientation of the ligands to each other as well as to the target molecule is derived from the structural data. That spatial orientation defines the distance between the binding sites of the two ligands and the orientation of each ligand to those sites.

Using that spatial orientation data, the two or more ligands are then linked together to form a new ligand. Linking is accomplished in a manner that maintains the spatial orientation of the ligands to one another and to the target molecule.

There are numerous advantages to the 1D-NMR-based discovery process of the present invention. First, because a process of the present invention identifies ligands by directly measuring binding to the target molecule, the problem of false positives is significantly reduced.

Second, the problem of false negatives is significantly reduced because the present process can identify compounds that specifically bind to the target molecule with a wide range of dissociation constants.

Third, the requirement for low-molecular weight (<40 kDa) $^{15}$N-labeled proteins which are stable at high concentrations, as required by methods utilizing $^{15}$N/$^{1}$H correlation spectroscopy, is eliminated using the present invention.

Fourth, the ability to directly identify active compounds in a mixture of compounds by comparison of known chemical shifts significantly reduces the amount of time required for screening and identifying active compounds that bind to the target molecule.

Because the signals of the potential ligands are monitored to detect binding to the target molecule, two or more ligands can be identified which bind simultaneously to the target molecule. The ability to simultaneously identify binding sites of different ligands allows a skilled artisan to 1) define negative and positive cooperative binding between ligands and 2) design new drugs by linking two or more ligands into a single compound while maintaining a proper orientation of the ligands to one another and to their binding sites.

In its principal aspect, the present invention provides a process of screening compounds to identify ligands that bind to a specific target molecule. That process comprises the steps of: a) generating a first $T_2$- or diffusion-filtered proton spectrum of one or a mixture of chemical compounds; b) exposing one or a mixture of chemical compounds to the target molecule; c) generating a second $T_2$- or diffusion-filtered proton spectrum of one or a mixture of chemical compounds that has been exposed the target molecule in step (b); and d) comparing said first and second $T_2$- or diffusion-filtered proton spectra to determine differences between said first and said second spectra, the differences identifying the presence of one or more compounds that are ligands which have bound to the target molecule.

Where a process of the present invention screens more than one compound in step (b) and where a difference between spectra is observed, the active compound can be identified by prior knowledge of the chemical shifts of the compounds in the mixture in the absence of the target molecule. In the absence of such information, additional steps are performed to identify which specific compound is binding to the target molecule. Those additional steps comprise the steps of e) generating a $T_2$- or diffusion-filtered proton spectrum of each compound in the mixture f) exposing each compound in the mixture individually to the target molecule, g) generating a $T_2$- or diffusion-filtered proton spectrum of each compound in the mixture after exposure to the target molecule h) comparing each spectrum generated in step g) to the first spectrum generated from the target molecule alone to determine differences in any of those compared spectra, the differences identifying the presence of a compound that is a ligand which has bound to the target molecule.

Any target molecule can be used in a process of the present invention, provided that the target molecule is sufficiently larger than the test compounds so as to cause large differences in relaxation or diffusion rates of the test compound upon binding to the target molecule. Because of the importance of proteins in medicinal chemistry, a preferred target molecule is a polypeptide. In a preferred embodiment, the target molecule is a polypeptide of molecular weight greater than 5 kDa.

The screening process of the present invention begins with the generation or acquisition of either a $T_2$-filtered or a diffusion-filtered one-dimensional proton spectrum of the compound or mixture of compounds. Means for generating $T_2$-filtered or diffusion-filtered one-dimensional proton spectra are well known in the art (see, e.g., S. Meiboom and D. Gill, *Rev. Sci. Instrum.* 29:688(1958), S. J. Gibbs and C. S. Johnson, Jr. *J. Main. Reson.* 93:395–402 (1991) and A. S. Altieri, et al. *J. Am. Chem. Soc.* 117: 7566–7567 (1995)).

To facilitate the acquisition of NMR data on a large number of compounds (e.g., a database of synthetic or naturally occurring small organic compounds), a sample changer is employed. Using the sample changer, a total of 60 samples can be run unattended. Thus, using the typical acquisition parameters (128 scans per free induction decay (fid), 100–120 spectra can be acquired in a 24 hour period.

To facilitate processing of the NMR data, computer programs are used to transfer and automatically process the multiple one-dimensional NMR data.

A representative one-dimensional $T_2$-filtered spectrum of mixture of compounds is shown in FIG. 1A. A representative one-dimensional diffusion-filtered spectrum of mixture of compounds is shown in FIG. 2A.

Following acquisition of the first spectrum, the labeled target molecule is exposed to one or more test compounds. Where more than one test compound is to be tested simultaneously, it is preferred to use a database of compounds such as a plurality of small molecules. Such molecules are typically dissolved in perdeuterated dimethylsulfoxide . The compounds in the database can be purchased from vendors or created according to desired needs.

Individual compounds can be selected inter alia on the basis of size (molecular weight=100–300) and molecular diversity. Compounds in the collection can have different shapes (e.g., flat aromatic rings(s), puckered aliphatic rings (s), straight and branched chain aliphatics with single, double, or triple bonds) and diverse functional groups (e.g., carboxylic acids, esters, ethers, amines, aldehydes, ketones, and various heterocyclic rings) for maximizing the possibility of discovering compounds that interact with widely diverse binding sites.

The NMR screening process of the present invention utilizes ligand concentrations ranging from about 0.05 to about 1.0 mM. At these concentrations, compounds which are acidic or basic can significantly change the pH of buffered protein solutions. Chemical shifts are sensitive to pH changes as well as direct binding interactions, and "false positive" chemical shift changes, which are not the result of ligand binding but of changes in pH, can therefore be observed. It is thus necessary to ensure that the pH of the buffered solution does not change upon addition of the ligand. One means of controlling pH is set forth below.

Compounds are stored at 263K as 1.0 and 0.1 M stock solutions in dimethylsulfoxide (DMSO). This is necessary because of the limited solubility of the ligands in aqueous solution. It is not possible to directly adjust the pH of the DMSO solution. In addition, HCl and NaOH form insoluble salts in DMSO, so alternative acids and bases must be used. The following approach has been found to result in stable pH.

The 1.0 M stock solutions in DMSO are diluted 1:10 in 50 mM phosphate, pH 7.0. The pH of that diluted aliquot solution is measured. If the pH of the aliquot is unchanged (i.e., remains at 7.0), a working solution is made by diluting the DMSO stock solution 1:10 to make a 0.1 M solution and that solution is stored.

If the pH of the diluted aliquot is less than 7.0, ethanolamine is added to the 1.0 M stock DMSO solution, that stock solution is then diluted 1:10 with phosphate buffer to make another aliquot, and the pH of the aliquot rechecked.

If the pH of the diluted aliquot is greater than 7.0, acetic acid is added to the 1.0 M stock DMSO solution, that stock solution is then diluted 1:10 with phosphate buffer to make another aliquot, and the pH of the aliquot rechecked.

Ethanolamine and acetic acid are soluble in DMSO, and the proper equivalents are added to ensure that upon transfer to aqueous buffer, the pH is unchanged. Adjusting the pH is an interactive process, repeated until the desired result is obtained.

Note that this procedure is performed on 1:10 dilutions of 1.0 M stock solutions (100 mM ligand) to ensure that no pH changes are observed at the lower concentrations used in the experiments (0.1 to 10 mM) or in different/weaker buffer systems.

Following exposure of the test compounds to the target molecule, a second one-dimensional $T_2$-or diffusion-filtered spectrum is generated. For the $T_2$-filtered approach, that second spectrum is generated in the same manner as set forth above. The first and second spectra are then compared to determine whether there are any differences between the two spectra. Differences in the one-dimensional $T_2$-filtered spectra indicate that the ligand is binding to the target molecule. Those differences are determined using standard procedures well known in the art. For the diffusion-filtered method, the second spectrum is generated by looking at the spectral differences between low and high gradient strengths—thus selecting for those compounds whose diffusion rates are comparable to that observed in the absence of target molecule.

By way of example, FIGS. 1A through 1E shows comparisons of one-dimensional $T_2$-filtered spectra before and after exposure of various target molecules to a mixture of test compounds, and the subsequent identification of an active compound. A detailed description of how these studies were performed can be found hereafter in Example 1.

Also by way of example, FIGS. 2A through 2F shows comparisons of one-dimensional diffusion-filtered spectra before and after exposure of various target molecules to a mixture of test compounds, and the subsequent identification of an active compound. A detailed description of how these studies were performed can be found hereinafter in Example 2.

To discover additional molecules that bind to the protein, molecules are selected for testing based on the structure/ activity relationships from the initial screen and/or structural information on the initial leads when bound to the protein. By way of example, the initial screening may result in the identification of ligands, all of which contain an aromatic ring. The second round of screening would then use other aromatic molecules as the test compounds.

Because of their importance in medicinal chemistry, a preferred target molecule for use in such a process is a polypeptide. In one preferred embodiment, a process of detecting the binding of one ligand to the target molecule can be performed in the presence of a second ligand. In accordance with this embodiment, the target molecule is bound to that second ligand before exposing that target to the test compounds.

Preferred target molecules, means for generating spectra, and means for comparing spectra are the same as set forth above.

The initial step in the design process is the identification of two or more ligands that bind to the specific target molecule. The identification of such ligands is done using one-dimensional $T_2$- or diffusion-filtered spectroscopy as set forth above.

Once two or more ligands are identified as binding to the target molecule at different sites, a complex between the target molecule and ligands is formed. Where there are two ligands, that complex is a ternary complex. Quaternary and other complexes are formed where there are three or more ligands.

Complexes are formed by mixing the target molecule simultaneously or sequentially with the various ligands under circumstances that allow those ligands to bind the target. Means for determining those conditions are well known in the art.

Once that complex is formed, structural data is obtained. Any means of obtaining structural data can be used. Such methods are well known in the art. Exemplary and preferred methods are NMR and X-ray crystallography.

An analysis of the structural data can reveal the spatial orientation of the ligands relative to each other as well as to the conformation of the target molecule. First, the spatial orientation of each ligand to the target molecule allows for identification of those portions of the ligand directly involved in binding (i.e., those portions interacting with the target binding site) and those portions of each ligand that project away from the binding site and which portions can be used in subsequent linking procedures.

Second, the spatial orientation data is used to map the positions of each ligand relative to each other. In other words, discrete distances between the spatially oriented ligands can be calculated.

Third, the spatial orientation data also defines the three-dimensional relationships amongst the ligands and the target. Thus, in addition to calculating the absolute distances between ligands, the angular orientations of those ligands can also be determined.

Knowledge of the spatial orientations of the ligands and target is then used to select linkers to link two or more ligands together into a single entity that contains all of the ligands. The design of the linkers is based on the distances and angular orientation needed to maintain each of the ligand portions of the single entity in proper orientation to the target.

The three-dimensional conformation of suitable linkers is well known or readily ascertainable by one of ordinary skill in the art. While it is theoretically possible to link two or more ligands together over any range of distance and three-dimensional projection, in practice certain linitations of distance and projection are preferred. In a preferred embodiment, ligands are separated by a distance of less than about 15 Angstroms (Å), more preferably less than about 10 Å and, even more preferably less than about 5 Å.

Once a suitable linker group is identified, the ligands are linked with that linker. Means for linking ligands are well known in the art and depend upon the chemical structure of the ligand and the linking group itself. Ligands are linked to one another using those portions of the ligand not directly involved in binding to the target molecule.

The following Examples illustrate preferred embodiments of the present invention and are not limiting of the specification and claims in any way.

EXAMPLE 1

Screening Compounds using $T_2$-filtered Spectroscopy

A. FKBP

Recombinant human FK binding protein (FKBP) was prepared as described in Logan et al., *J. Mol. Biol.*, 236: 637–648 (1994).

The pulse sequence employed for exploiting the changes in transverse ($T_2$) relaxation rates of potential ligands in the presence of the target molecule is the Carr-Purcell-Meiboom-Gill (CPMG) sequence as described in S. Meiboom and D. Gill, *Rev. Sci. Instrum.* 29:688 (1958).

The present invention takes advantage of the fact that large molecules or complexes of molecules which tumble slowly in solution will have shorter transverse ($T_2$) relaxation times than a small molecule which tumbles rapidly in solution. This is well-known in the art. The present invention takes advantage of the fact that a small molecule, which normally tumbles rapidly when free in solution, will tumble more slowly when bound to a larger target molecule. Thus, the transverse ($T_2$) relaxation rates of the small molecule will change (decrease) when bound to a target molecule.

This is demonstrated in FIGS. 1A through 1E for FKBP and compound 1, which binds to FKBP with an affinity of 200 $\mu$M. In FIG. 1A, a CPMG sequence with a spin-lock time of 200 ms is applied to the compound in the absence of FKBP. Since the transverse relaxation rates of small molecules free in solution are generally on the order of seconds, negligible relaxation occurs during the spin-lock time, and the signals of the free ligand are observed. In the presence of FKBP, however, the ligand signals are significantly reduced after the spin lock time, and only residual protein and ligand peaks remain in the spectrum, as shown in FIG. 1B. These differences can be detected either by direct inspection, or by a spectral differencing method in which the spectrum of FKBP alone (after the spin-lock, FIG. 1C) is subtracted from the spectrum of the compound in the presence of FKBP (also after the spin-lock, FIG. 1B), resulting in the spectrum shown in FIG. 1D. This spectrum then contains only the residual ligand peaks, which, if desired, can be even further reduced in intensity by the application of longer spin-lock times. This spectrum (FIG. 1D) is then subtracted from the spectrum of the test compound alone (FIG. 1A), resulting in the spectrum shown in FIG. 1E. The positive peaks in the difference spectrum correspond to the chemical shifts of the compound in the absence of target protein, as demonstrated by a comparison of FIG. 1A with FIG. 1E, while the negative peaks correspond to the chemical shifts of the compound when bound to FKBP. This information can be used to identify the active compound.

The same experiments can be performed on a mixture of compounds. In these experiments, compounds 2–9, which are known not to bind to FKBP, were combined with compound 1. FIGS. 2A through 2F shows the $T_2$-filtered spectra for the mixture of compounds in the absence of FKBP (FIG. 2A), the presence of FKBP (FIG. 2B), and for FKBP alone (FIG. 2C). The spectrum in FIG. 2D, obtained by subtracting FIG. 2C from FIG. 2B, contains the resonances of the ligands in the presence of the protein. The spectrum in FIG. 2E, obtained by subtracting FIG. 2D from FIG. 2A, contains positive peaks which correspond to the positions of the reonances of compound 1 in the absence of FKBP, as demonstrated in the reference spectrum shown in FIG. 2F. The chemical shift information contained in FIG. 2E is used not only to detect the presence of a ligand which binds to the protein, but can also be used to identify which compound in the mixture of compounds is binding, provided that such chemical shift information about the free ligands is known a priori.

FIGS. 3A through 3E shows the same set of experiments with a mixture of compounds 2-9 only, which do not bind to FKBP. As observed in FIG. 3E, no positive, absorptive ligand resonances are observed in the difference spectrum, indicating that no ligands are binding to FKBP.

EXAMPLE 2
Screening Compounds using Diffusion-filtered Spectroscopy
A. FKBP

The pulse sequence employed for exploiting the changes in diffusion rates of potential ligands in the presence of the target molecule that described by S. J. Gibbs and C. S. Johnson, Jr. *J. Main. Reson.* 93:395–402 (1991) and A. S. Altieri, et al. *J. Am. Chem. Soc.* 117: 7566–7567 (1995).

The present invention takes advantage of the fact that small molecules diffuse more rapidly than larger molecules in solution. This is well-known in the art. The present invention takes advantage of the fact that a small molecule, which normally diffuses rapidly when free in solution, will diffuse more slowly when bound to a larger target molecule. Thus, the diffusion rates of the small molecule will change (decrease) when bound to a target molecule.

The ability to detect ligand binding using diffusion filters is demonstrated for FKBP binding to compound 1, as shown in FIGS. 4A through 4E. First, diffusion filtered spectra are obtained at weak and strong gradient strengths on a sample of compound 1 in the presence of FKBP (FIGS. 4A and 4B, respectively). These spectra are then subtracted to produce the spectrum shown in FIG. 4C. This spectrum contains residual ligand resonances of compound 1. This spectrum is then subtracted from a reference spectrum of compound 1 alone (after a weak gradient, FIG. 4D), to yield a spectrum containing the resonances of the ligand which binds to the protein (FIG. 4E). As with the $T_2$-filtered experiment, the positive peaks in FIG. 4E correspond to the chemical shifts of the ligand in the absence of protein, while the negative peaks correspond to the chemical shifts of the compound when bound to FKBP. This information can be used to identify the active compound.

The same experiments can be performed on a mixture of compounds. In these experiments, compounds 2–9, which are known not to bind to FKBP, were combined with compound 1. FIGS. 5A and 5B show spectra of the mixture of compounds on the presence of FKBP after weak and strong gradient strengths, respectively. The difference between these spectra produces a spectrum (FIG. 5C). Subtracting this spectrum from a control spectrum of the mixture of ligands in the absence of FKBP (after a weak gradient, FIG. 5D), yields a spectrum (FIG. 5E) which contains positive resonances at the chemical shifts for compound 1 in the absence of FKBP (FIG. 5F). The chemical shift information contained in FIG. 5E is used not only to detect the presence of a ligand which binds to the protein, but can also be used to identify which compound in the mixture of compounds is binding, provided that such chemical shift information about the free ligands is known a priori.

FIGS. 6A through E shows the same set of experiments with a mixture of compounds 2-9 only, which do not bind to FKBP. As observed in FIG. 6E, no positive ligand resonances are observed in the difference spectrum, indicating that no ligands are binding to FKBP.

All NMR spectra were recorded at 300K on a Bruker AMX500 NMR spectrometer. All spectra were recorded with 256 scans and a proton sweep width of 8333.3 Hz and a proton 90 degree pulse length of 7 $\mu$s. For the $T_2$-filtered experiments, the spin-lock time was 200 ms with a spin-echo delay of 1 ms. For the gradient-filtered spectra, low and high gradient strengths correspond to 3 and 48 Gauss/cm, respectively, and a diffusion delay time of 300 ms was used. In all experiments, the concentration of each ligand was 100 $\mu$M, the concentration of FKBP was 50 $\mu$M, and the buffer was 50 mM $PO_4$, 100 mM NaCl, pH 6.5 (95% D20). The NMR data were processed and analyzed on Silicon Graphics computers.

The above examples are non-limiting and the present invention is also directed to a process of designing a high-affinity ligand which is the linked combination of at least two ligands found in the example as presented above.

TABLE 1

| No. | Compound | $K_D$ (mM)[a] |
|---|---|---|
| 1 | | 0.2 |
| 2 | | >10 |
| 3 | | >10 |
| 4 | | >10 |
| 5 | | >10 |
| 6 | | >10 |

TABLE 1-continued

| No. | Compound | $K_D$ (mM)[a] |
|---|---|---|
| 7 | [structure: methoxy-biphenyl-CO2H] | >10 |
| 8 | [structure: bithiophene-CO2H] | >10 |
| 9 | [structure: 4-hydroxy-3-phenylcoumarin] | >10 |

[a]The $K_D$ for compound 1 was obtained from S. Shuker, et al., Science 274:1531–1534 (1996), while those for compounds 2–9 were estimated from the absence of observed chemical shift changes in $^{15}$N—HSQC spectra of FKBP at compound concentrations of 1.0 mM, as described in the same reference.

What is claimed is:

1. A process of screening compounds to identify compounds that are ligands that bind to a specific target molecule comprising the steps of:
   a) generating a first one-dimensional $T_2$- or diffusion-filtered NMR spectrum of one or a mixture of chemical compounds;
   b) exposing the compound or a mixture of chemical compounds to a target molecule;
   c) generating a second one-dimensional $T_2$- or diffusion-filtered spectrum of one or a mixture of chemical compounds that has been exposed to the target molecule (b); and
   d) comparing said first and second one-dimensional $T_2$- or diffusion-filtered spectra to determine differences between said first and
      said second spectra, the differences identifying the presence of one or more compounds that are ligands which have bound to the target molecule.

2. The process of claim 1 wherein a mixture of chemical compounds is used in (b), further comprising the steps subsequent to step d) of
   e) generating a first one-dimensional $T_2$- or diffusion-filtered spectrum of each compound in the mixture;
   f) exposing each compound of said mixture individually to the target molecule,
   g) generating a second one-dimensional $T_2$- or diffusion-filtered spectrum of each compound that has been exposed to the target molecule in step (f); and
   h) comparing each spectrum generated in step g) to said first spectrum to determine differences in any of those compared spectra, the differences identifying the presence of a compound that is a ligand which has bound to the target molecule.

3. The process of claim 1 further comprising the step of binding the target molecule to a second ligand before step (a).

4. The process of claim 1, wherein the screened compounds are selected from a compound collection of diverse small molecules.

5. The process of claim 1 wherein the target molecule is a polypeptide.

6. The process of claim 5 wherein the polypeptide is selected from an enzyme or a receptor.

7. The process of claim 1 wherein the target molecule is a polynucleic acid.

8. The process of claim 1 wherein the target molecule is unlabeled.

9. A process of designing a high-affinity ligand to a target molecule, comprising
   (a) identifying a first ligand to the target molecule using one-dimensional T2 or diffusion-filtered NMR spectroscopy;
   (b) identifying one or more additional ligands to the target molecule using one-dimensional T2 or diffusion-filtered NMR spectroscopy;
   (c) forming a complex between the first identified ligand and the one or more additional identified ligands with the target molecule;
   (d) determining the three-dimensional structure of at least that portion of the complex wherein the first and one or more additional ligands are binding to the target molecule and, thus, the spatial orientation of the first and one or more additional ligands on the target molecule; and
   (e) linking the first and one or more additional ligands to maintain the spatial orientation determined in step (d) to form the high-affinity ligand.

10. A process according to claim 9 wherein the target molecule is a polypeptide.

11. A process according to claim 9 wherein the target molecule is unlabeled.

12. A process according to claim 9 wherein the first and one or more additional ligands are selected from a pool of diverse small molecules.

13. A process according to claim 12 wherein the small molecules are selected from a compound collection.

14. A process according to claim 9 wherein the complex is formed by combining the first and one or more additional ligands with the target molecule in solution.

15. A process according to claim 14 wherein the complex formed in solution is similar to or identical to the complex formed between the ligand or one or more additional ligands under physiological conditions.

16. A process according to claim 9 wherein the ligand and one or more additional ligands are linked together by a convergent or linear organic synthesis to form the high-affinity ligand.

17. A process according to claim 9 wherein the high-affinity ligand is a pharmaceutically active moiety.

* * * * *